United States Patent [19]

Curelaru et al.

[11] Patent Number: 4,581,019

[45] Date of Patent: Apr. 8, 1986

[54] DEVICE FOR INTRODUCING A CATHETER-CANNULA INTO A BLOOD VESSEL

[76] Inventors: Ioan Curelaru, Dr. Lindsgatan 3, Göteborg, Sweden, 413 25; Bengt Gustavsson, Bergsbogatan 29, Göteborg, Sweden, 421 79; Lars-Erik Linder, Valebergsgaten 319, Billdal, Sweden, 427 00

[21] Appl. No.: 456,047

[22] PCT Filed: Apr. 22, 1982

[86] PCT No.: PCT/SE82/00127

§ 371 Date: Dec. 21, 1982

§ 102(e) Date: Dec. 21, 1982

[87] PCT Pub. No.: WO82/03558

PCT Pub. Date: Oct. 28, 1982

[30] Foreign Application Priority Data

Apr. 23, 1981 [SE] Sweden ............................ 8102576

[51] Int. Cl.[4] ........................ A61M 5/00; A61M 25/00
[52] U.S. Cl. ..................................... 604/164; 604/280
[58] Field of Search ............................... 604/158–170, 604/280

[56] References Cited

U.S. PATENT DOCUMENTS

| 3,382,872 | 5/1968 | Rubin ............................... 604/161 X |
| 3,565,074 | 2/1971 | Foti ..................................... 604/164 |
| 3,713,442 | 1/1972 | Walter ................................ 604/161 |
| 3,902,501 | 9/1975 | Citron et al. ................. 128/419 PX |
| 4,166,469 | 9/1979 | Littleford ...................... 604/164 X |
| 4,306,562 | 12/1981 | Osborne ......................... 604/280 |
| 4,402,685 | 9/1983 | Buhler et al. ...................... 604/280 |
| 4,451,256 | 5/1984 | Weikl et al. ...................... 604/164 |
| 4,473,067 | 9/1984 | Schiff ............................. 128/1 D |

FOREIGN PATENT DOCUMENTS

82/03558 10/1982 PCT Int'l Appl. .................. 604/53

Primary Examiner—Dalton L. Truluck
Attorney, Agent, or Firm—Holman & Stern

[57] ABSTRACT

The present invention discloses a device for introducing soft, short, catheter-cannula into a blood vessel. The device comprises a puncturing member and a connection member arranged at the rear end of the catheter cannula remote from the blood vessel. The device is easy to handle and the insertion of the needle, the catheter and the introducer is made in a single step.

12 Claims, 15 Drawing Figures

DEVICE FOR INTRODUCING A CATHETER-CANNULA INTO A BLOOD VESSEL

BACKGROUND OF THE INVENTION

The present invention refers to a device for introducing soft short catheter-cannulas into a blood-vessel by means of a puncturing member for puncturing the blood-vessel, a connection member being arranged at the rear end of the catheter-cannula remote from the blood-vessel as seen during its use.

Plastic catheter-cannula inserted into a blood-vessel are used to a great extent for sampling of blood and administration of drugs, fluid and blood. They have the advantage over steel needles because they do not easily cause vessel and tissue injuries and haematoma formation when the patient moves.

A serious side-effect of plastic catheter-cannulas, however, is the high incidence of thrombosis and thrombophlebitis.

Thrombosis induced by contact with blood of plastic surfaces is a major unsolved problem and a great number of factors are probably involved. It has been repeated however that soft catheter-cannulas, especially those made of silicone elastomers are less thrombogenic than catheter-cannulas made of a stiffer material, e.g. PVC, polyethylene, Teflon$^R$.

These soft catheter-cannulas are however very difficult to insert into a blood-vessel as they easily bend and get twisted.

In order to facilitate vascular insertion of long, soft catheter-cannulas a number of methods are proposed, which however are not adapted for short catheter-cannulas, owing to the limitation on one hand are traumatic for small, peripheral veins and arteries and on the other hand they are expensive and cumbersome.

Among these methods can be mentioned the use of stiff introducer-cannulas made of, for example Teflon$^R$, surgical methods, use of a steel winged needle through which the catheter-cannula is inserted and which splits longitudinally when it is removed from the vessel.

In the European patent application No. 0.021.446 there is described an introducer-cannula of stiff plastic provided with longitudinal lines of weakness and intended for the insertion of long catheter-cannulas in a blood-vessel. After insertion of the catheter-cannula the introducer-cannula is withdrawn and removed from the catheter-cannula by severing its two halves along the lines of weakness. This device is however only adapted for long catheter-cannulas and not for the insertion of soft, short catheter-cannulas into veins and arteries.

There is however a method presently in use and adapted for insertion of short, soft catheter-cannulas. The method is developed by VICRA, a division of Travenol Laboratories, USA. The device used comprises a longitudinally slotted needle which permits the insertion of a 5 cm long silicone elastomer catheter-cannula armoured with a metal spring stylet. After insertion of the catheter-cannula the needle and the stylet are withdrawn.

Both device and method are however not without problem. Vein puncture is difficult and traumatic because of the slotted needle which has a diameter significantly larger than that of the silicone eleastomer catheter-cannula, withdrawal of the metal spring stylet may sometimes be difficult and the device may be expensive.

In the European patent application No. 0.002.607 there is described a device for implanting a pacemaker electrode through the subclavion vein into the heart. The device comprises an introducer sleeve arranged on the outside of the needle and provided with a longitudinal line of weakness along which the introducer sleeve can be severed and removed from the body when the electrode has been placed in the desired position.

The device is adapted for insertion of long, rigid implants (pacemaker electrodes) through the subclavion vein and is not adapted for insertion of soft, short catheter-cannulas into peripheral veins and arteries.

SUMMARY AND ADVANTAGES OF THE INVENTION

The purpose of the present invention is to provide a device mainly intended for insertion of soft, short catheter-cannulas into peripheral veins and arteries. The device must be easy to handle, the catheter-cannula must be given support during the insertion, and said support must be easily removable from the catheter-cannula when this is located in the desired position in the vessel. This has been achieved by the fact that an introducer-cannula is arranged on the outside of the catheter-cannula and extending over the substantial length of and being stiffer than the catheter-cannula, said introducer-cannula being intended to be introduced into the blood-vessel together with the catheter-cannula and said introducer-cannula being severed or severable along its length and at its rear end provided with at least one gripping member or the like for removing the introducer-cannula from the catheter-cannula.

DESCRIPTION OF THE DRAWINGS

The invention will now be described in detail with reference to some embodiments shown in the accompanying drawing.

DESCRIPTION OF THE EMBODIMENT

Figure 1:
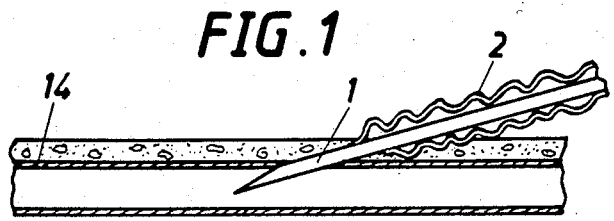
FIG. 1 is a section illustrating what would happen if one tries to introduce a soft catheter-cannula into a blood-vessel only by means of a needle.

In FIG. 1 is illustrated what would happen if one tries to introduce a catheter-cannula 2 of a soft plastic material, e.g. silicone elastomer or polyurethane, passed on a needle into a peripheral blood-vessel 14. The catheter-cannula 2 will not be introduced into the blood-vessel but instead be sagged on the needle.

Figure 3:
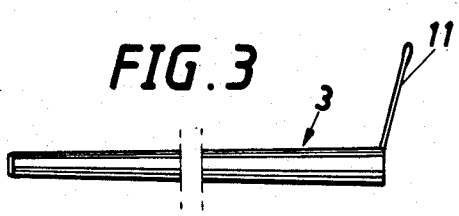
FIG. 3 is a side view of an embodiment of the introducer-cannula according to the invention.
Figure 4:
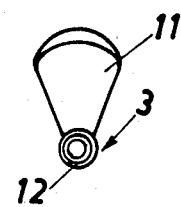
FIG. 4 is a front view of the introducer-cannula according to FIG. 3.

An outer rigid support is, therefore, necessary for enabling the insertion of such a soft catheter-cannula into a blood-vessel. According to the embodiment shown in FIGS. 2-4 this outer support is provided by an introducer-cannula 3 of a rigid and resilient plastic material. The introducer-cannula 3 is on its inferior side provided with a slit 12 extending along the entire length thereof. The introducer-cannula 3 has to be made of a material which is resilient enough for keeping the edges of the slit 12 pressed against each other.

Figure 2:
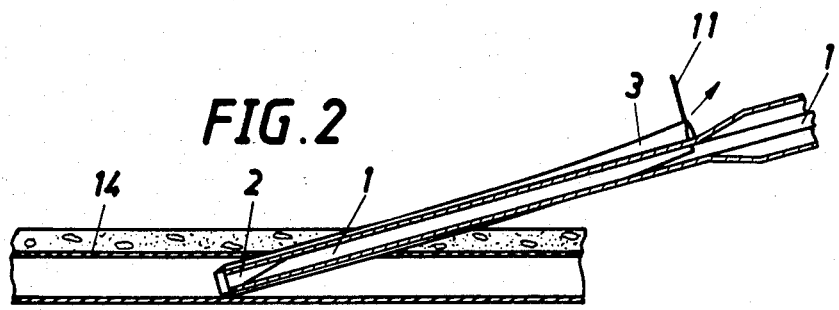
FIG. 2 is a corresponding section showing a device according to the invention in a position where the introducer-cannula is being withdrawn from the catheter-cannula.

The introducer-cannula 3 is at its outer end provided with a gripping member 11 in the form of an upright flap by means of which the introducer-cannula can be withdrawn from the catheter-cannula 2 and the blood-vessel 14 as is shown in FIG. 2.

Figure 5:
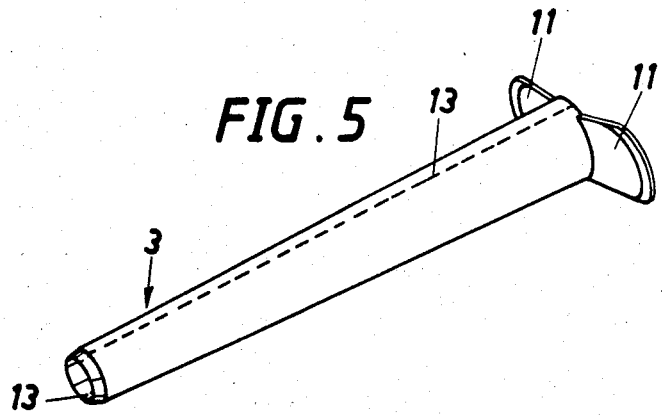
FIG. 5 is a perspective view of another embodiment of the introducer-cannula.

In the embodiment shown in FIG. 5 the introducer-cannula 3 has two diametrically opposed longitudinal lines of weakness 13, e.g. grooves, perforations or the like, and two gripping members 11 by means of which the introducer-cannula 3 can be severed along the lines of weakness 13.

Figure 6:
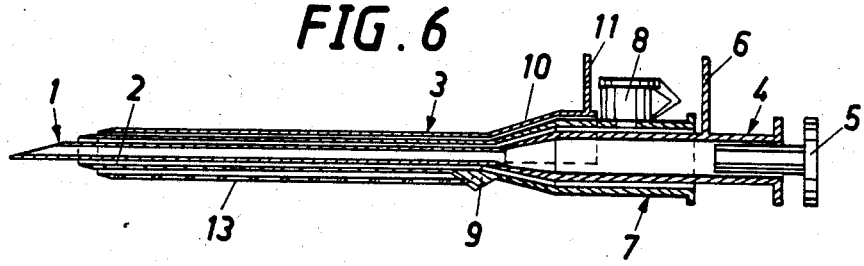
FIG. 6 is a longitudinal section through a further embodiment of the invention.
Figure 7:
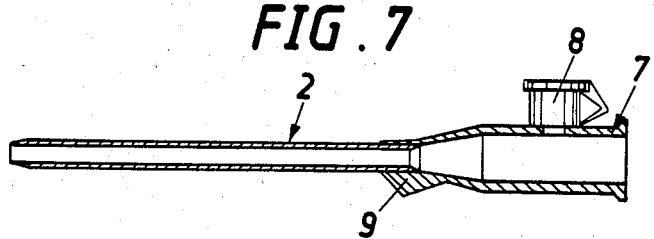
FIG. 7 is a longitudinal section through the catheter-cannula according to FIG. 6.
Figure 8:
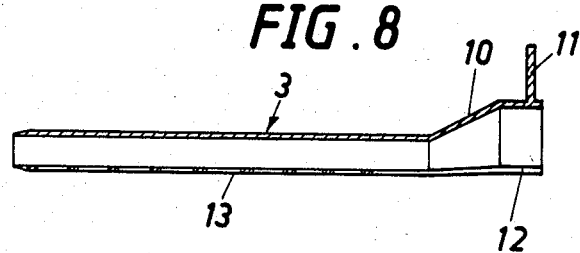
FIG. 8 is a longitudinal section through the introducer-cannula according to FIG. 6.

In FIG. 6 is shown another embodiment together with a conventional needle 1. The needle 1 is at its end remote from the tip provided with a plastic hub 4 provided with a connection opening closed by a plug 5. The hub 4 is also provided with an upright flap 6 constituting a support for the thumb when the needle 1 is inserted into the blood-vessel.

The catheter-cannula 2 is tightly arranged on the outside of the needle 1. A connection member 7 is arranged at the end of the catheter-cannula 2 remote from the blood-vessel as seen in the position of use, said connection member 7 being in contact with the flap 6 of the hub 4. The connection member 7 is at its upper side provided with a connection opening 8 for the connection of a syringe. At the underside of the end facing the catheter-cannula 2 the connection member is provided with an edge-provided means or knife 9, which e.g. can have the shape of a rhombic pyramid. The connection member 7 is further provided with a pair of wings projecting laterally (shown in FIG. 13). The introducer-cannula 3 is arranged on the outside of the catheter-cannula 2 and extends over the substantial length thereof and has an inner diameter approximately equal to the outer diameter of the catheter-cannula 2. The wall thickness should preferably be as low as about 0.2 mm. The effective length of the catheter-cannula as well as the introducer-cannula is about 5 cm. Preferably the tip of the catheter-cannula overpasses that of the introducer-cannula by some mm in order to avoid that the retraction of the introducer-cannula from the vessel will be followed by that of the catheter-cannula. It can however prove to be suitable to have the tip of the introducer-cannula 3 overpass that of the catheter-cannula 2 instead. It has to be pointed out that the different components are shown on an enlarged scale for the sake of clarity. Besides the components 1, 2 and 3 which in reality are tight to each other are shown spaced from each other.

The introducer-cannula 3 has at its outer end an enlarged portion 10 extending over a part of the connection member 7 of the catheter-cannula 2. Said portion 10 is provided with an upright flap 11 making a support for the index finger when the whole device comprising needle 1, catheter-cannula 2 and introducer-cannula 3 is introduced into the vessel. The flap 11 also makes a support for the index finger and the thumb when the introducer-cannula 3 is withdrawn from the vessel.

The enlarged portion 10 of the introducer-cannula 3 is on its underside provided with a longitudinal slit 12 closing up in a point and continued by a longitudinal line of weakness 13, e.g. a groove, perforation or the like. The introducer-cannula can however lach the line of weakness if its walls are thin enough to be easily slotted by the knife 9. The knife 9 is located in the slit 12 and projects therefrom.

The device is used in the following way. The blood vessel, a peripheral vein or artery, e.g. on the back of the hand, is punctured by means of the needle 1 and the complex comprising needle 1, catheter-cannula 2 and introducer-cannula 3 is introduced into the vessel by pressing the thumb against the flap 6 of the hub 4, while the flap 11 of the introducer-cannula 3 form a support for the index finger. The needle 1 and the introducer-cannula 3 form rigid inner and outer resp. supports for the catheter-cannula 2 along the entire length thereof during the insertion.

When the catheter-cannula 2 has been placed in the desired position the introducer-cannula 3 is withdrawn from the vessel by drawing up and dorsally its flap 11, while the index finger and thumb of the other hand hold the hub 4 of the needle and the long finger and ring finger keep in place the catheter-cannula 2 by gripping the wings (shown in FIG. 13) of the connection member 7. The introducer-cannula 3 will during its withdrawal be splitted by the knife 9 along the line of weakness if any.

The splitting of the introducer-cannula 3 starts immediately as its withdrawal, i.e. when it is still located in the vessel.

According to a modified embodiment the knife 9 is located obliquely in relation to the axial direction of the device, at which the introducer-cannula 3 will be splitted along a helical line which would further facilitate its withdrawal from the catheter-cannula 2 and the vessel.

When the introducer-cannula 3 has been withdrawn the needle 1 is withdrawn from the catheter-cannula 2. In order to avoid the leakage of blood around and through the catheter-cannula 2 one can press with the finger the tip together located in the vessel.

A portion of the catheter-cannula 2, approximately 5 mm, should be located outside the body and the device is fastened to the skin by adhesive tapes.

Figure 9:
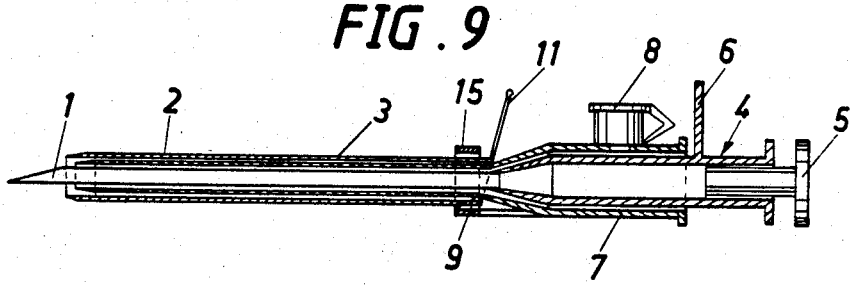
FIG. 9 is a longitudinal section through a further embodiment of the invention.

According to the embodiment shown in FIG. 9 the knife 9 is arranged on a ring-shaped member 15 connected with the connection member 7 of the catheter-cannula 2 and located before this so that the introducer-cannula extends through said ring 15. By placing the knife forward in this way as compared to the above embodiments the withdrawal of the introducer-cannula 3 is facilitated. Besides, the ring 15 provides a support for the introducer-cannula when 16 is withdrawn upwards-backwards.

Figure 10:
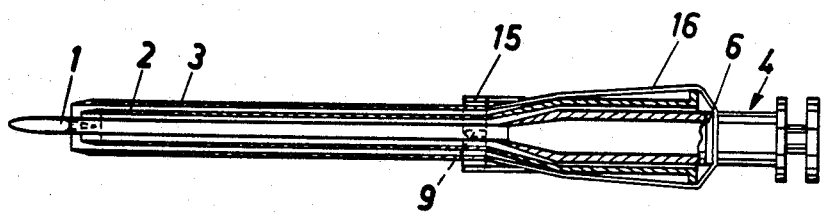
FIG. 10 is a section through another embodiment.
Figure 11:
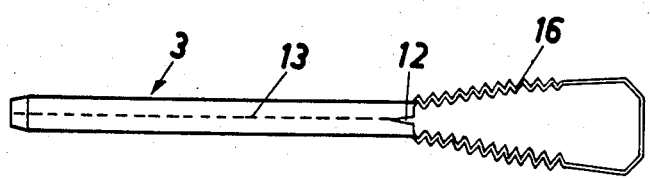
FIG. 11 shows the introducer-cannula according to FIG. 10.

According to the embodiment shown in FIGS. 10 and 11 a connecting member 16 is arranged between the introducer-cannula 3 and the needle hub 4, for providing a simultaneous withdrawal of the needle 1 and the introducer-cannula 3 from the catheter-cannula 2. The connecting member 16 consists of a loop, threads or the like extending from the rear end of the introducer-cannula 3 and attached to or around the flap 6 of the hub 4. In FIG. 11 is shown that the thread 16 is folded for admitting the introducer-cannula 3 and catheter-cannula 2 to be introduced a further distance into the blood-vessel than the needle 1.

Figure 12:
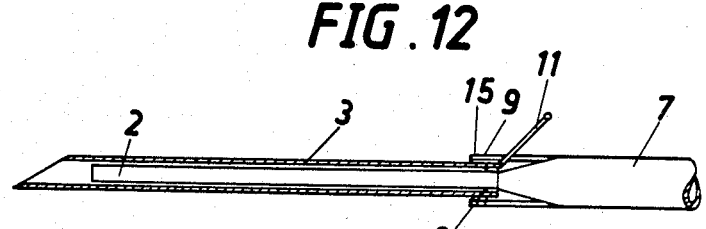
FIG. 12 is a section through a further embodiment.

In FIG. 12 there is shown an embodiment where the introducer-cannula 3 has been provided with a tip and constitutes the puncturing means or needle. The introducer-cannula 3 is in this embodiment provided with two longitudinal lines of weakness, and thus two knives 9 are arranged on the ring 15 projecting from the connection member 7 of the catheter-cannula.

Figure 13:
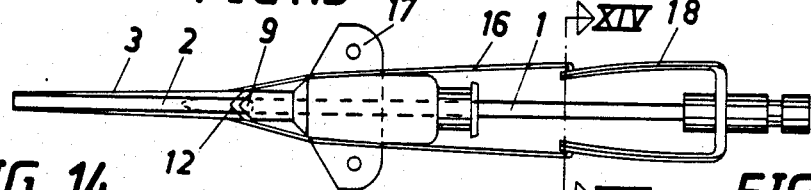
FIG. 13 is a section through a further embodiment.
Figure 14:
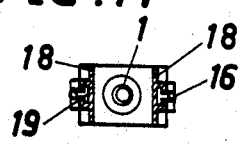
FIG. 14 is a section according to the line XIV—XIV in FIG. 13.

According to the embodiment shown in FIGS. 13 and 14 the needle hub 4 is provided with a pair of forwards projecting flaps 18, on the external sides of which guides 19 for the ends of the connecting threads 16 are formed. After the insertion of the introducer-cannula 3 and the catheter-cannula 2 into the blood-vessel by means of the needle 1, this can be kept still while the introducer-cannula and like catheter-cannula are inserted a further distance into the vessel, at which position the ends of the connecting threads 16 are displaced in the guides 19 to the position shown in FIG. 13. At the withdrawal of the needle 1, the introducer-cannula 3 will also be withdrawn from the catheter-cannula 2.

Figure 15:
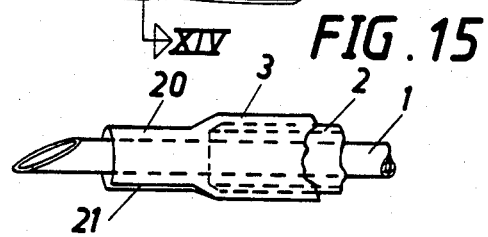
FIG. 15 is a perspective view of a modified insertion end of the introducer-cannula.

In FIG. 15 there is shown an embodiment where the insertion end of the introducer-cannula 3 is thinner than the rest of the introducer-cannula for facilitating the introduction. This thinner portion 20 is slotted, said slit 20 forming a continuation of the slit 12 or the line of weakness 13 in order to facilitate the withdrawal of the introducer-cannula 3.

It is of course within the scope of the invention to replace and combine parts of the embodiments shown with each other in different ways. Other modifications of the embodiments are also possible within the scope of the claims.

We claim:

1. A device for introducing soft short catheter-cannulas into a blood-vessel comprising a cannula for puncturing the blood-vessel, said catheter cannula being arranged on the outside of said cannula and being intended to be introduced into the blood-vessel together with the cannula, a connection member being arranged at the rear end of the catheter-cannula remote from the blood-vessel when in use, wherein an introducer-cannula is arranged on the outside of the catheter-cannula and extending over the substantial length of and being stiffer than the catheter-cannula, said introducer-cannula being intended to be introduced into the blood-vessel together with the catheter-cannula and the cannula, said introducer-cannula being severable along its length and at its rear end provided with at least one gripping member by means of which the introducer-cannula is withdrawn from the blood-vessel and removed from the cather-cannula under simultaneous severance.

2. The device according to claim 1, wherein said connection member of the catheter-cannula is provided with at least one severing means for severing the introducer-cannula when this is withdrawn and removed from the blood-vessel after the introduction of the catheter-cannula to the desired position.

3. The device according to claim 2, wherein the severing means consists of an edge, against which the introducer-cannula is intended to be opened or splitted respectively when it is withdrawn from the blood-vessel.

4. The device according to claim 2 wherein the introducer-cannula at its rear end remote from the blood-vessel as seen during use is provided with a slit and so arranged in relation to the connection member of the catheter-cannula (2) that said severing means is located in said slit.

5. The device according to claim 4, wherein the introducer-cannula is provided with at least one longitudinal line of weakness connecting on to said slit (12) in axial direction.

6. The device according to claim 4, wherein the introducer-cannula is provided with a helical line of weakness extending over its length and connecting on to said slit.

7. The device according to claim 6, wherein the severing means is arranged at an angle with the axial direction of the device.

8. The device according to claim 1, wherein the introducer-cannula is provided with a slit extending over its entire length and that the introducer-cannula is made of a resilient material which keeps the edges of the slit pressed against each other.

9. The device according to claim 8 wherein the introducer-cannula is passed through a ring-shaped member close to its rear end, said ring-shaped member being connected with the connection member of the catheter-cannula and providing support for the introducer-cannula at its withdrawal from the catheter-cannula.

10. The device according to claim 9, wherein said ring-shaped member is provided with said severing means.

11. The device according to claim 10, wherein at least one connecting member is arranged for connecting the rear end of the introducer-cannula with hub of the cannula for providing simultaneous withdrawal of the cannula and the introducer-cannula from the catheter-cannula.

12. The device according to claim 11, wherein said connecting member is limitedly displaceably attached to the hub of the cannula in the longitudinal direction thereof.

* * * * *